United States Patent [19]

Farge et al.

[11] 4,261,992

[45] Apr. 14, 1981

[54] ISOQUINOLINE DERIVATIVES

[75] Inventors: Daniel Farge, Thiais; Alain Jossin, St-Cloud; Gerard Ponsinet, Sucy-en-Brie; Daniel Reisdorf, Thiais, all of France

[73] Assignee: Rhone Poulenc Industries, Paris, France

[21] Appl. No.: 147,121

[22] Filed: May 6, 1980

[30] Foreign Application Priority Data

May 9, 1979 [FR] France ................ 79 11706

[51] Int. Cl.³ ................ C07D 417/12; A61K 31/54; C07D 417/14
[52] U.S. Cl. ................ 424/246; 544/32
[58] Field of Search ............ 424/246; 544/32

[56] References Cited

U.S. PATENT DOCUMENTS

| 4,188,482 | 2/1980 | Zinnes et al. ............ 544/32 |
| 4,189,480 | 2/1980 | Farge et al. ............ 544/32 |

*Primary Examiner*—John M. Ford
*Attorney, Agent, or Firm*—Stevens, Davis, Miller & Mosher

[57] ABSTRACT

Isoquinoline derivatives of the formula:

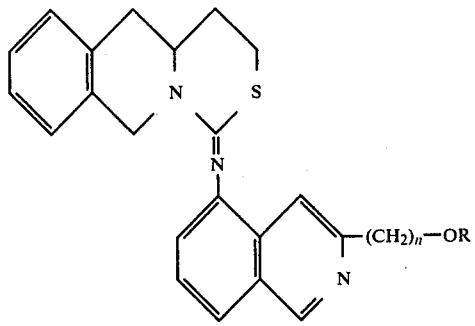

wherein R represents alkyl of 1 through 8 carbon atoms, and n represents 1 or 2, and their non-toxic pharmaceutically acceptable acid addition salts, are new compounds possessing useful pharmacological properties. They are particularly valuable as analgesic agents; some of them are also useful as anti-inflammatory and antipyretic agents.

9 Claims, No Drawings

ISOQUINOLINE DERIVATIVES

This invention relates to new therapeutically useful isoquinoline derivatives, to processes for their preparation and pharmaceutical compositions containing them.

In the specification of our U.S. Patent Application Ser. No. 958,617 filed Nov. 8, 1978 now U.S. Pat. No. 4,189,480 (and also in British Patent Application No. 43907/78—published under the Ser. No. 2007660) there are described and claimed isoquinoline derivatives of the general formula:

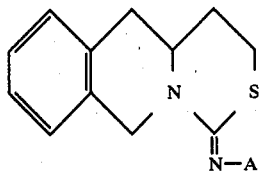

I wherein the symbol A represents a pyrid-3-yl or isoquinol-5-yl radical or a 3-alkylisoquinol-5-yl radical in which the alkyl moiety contains 1 to 10 carbon atoms in a straight or branched chain, and pharmaceutically acceptable acid addition salts thereof, which possess useful pharmacological properties and are, in particular, active as analgesic, anti-inflammatory and antipyretic agents.

As a result of further research and experimentation it has now been found that related compounds wherein the symbol A represents a 3-alkoxyalkylisoquinol-5-yl grouping of the general formula:

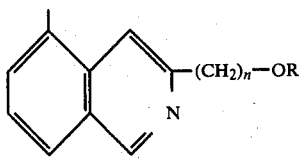

II wherein R represents a straight- or branched chain alkyl radical containing 1 to 8 carbon atoms and n represents 1 or 2, also possess useful pharmacological properties.

The present invention accordingly provides new isoquinoline derivatives of the general formula:

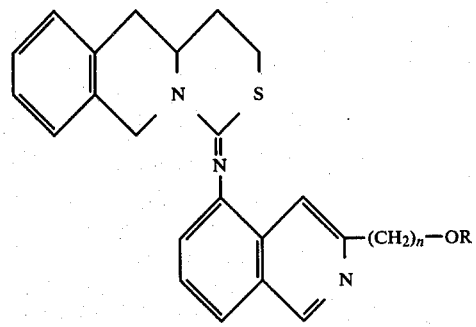

III wherein R and n are as hereinbefore defined, and acid addition salts thereof.

The compounds of general formula III can exist in (R) and (S) forms and the invention includes both such forms and mixtures thereof.

The compounds of general formula III can be prepared by application of processes disclosed in our aforementioned patent application.

Thus they can be prepared, according to a feature of the present invention, by the process which comprises the cyclisation of a 1,2,3,4-tetrahydroisoquinoline of the general formula:

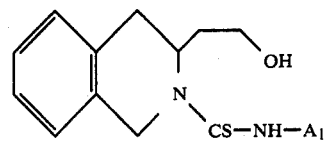

IV wherein $A_1$ represents a grouping of general formula II depicted above.

The cyclisation can be carried out either directly by heating in an acid medium, in which case the reaction is advantageously carried out at a temperature between 90° and 100° C. in an aqueous solution of an inorganic acid, e.g. in hydrochloric acid, or by the action of methanesulphonyl chloride or tosyl chloride in an organic solvent, such as pyridine, at a temperature of about 20° C., after which the intermediate formed of the general formula:

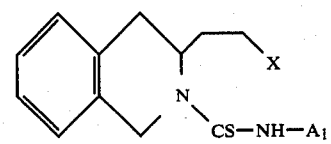

V (wherein $A_1$ is as hereinbefore defined, and X represents the methanesulphonyloxy or tosyloxy radical) is heated at a temperature between 60° and 120° C. in dimethylformamide.

The 1,2,3,4-tetrahydroisoquinolines of general formula IV can be obtained by the reaction of an isothiocyanate of the general formula:

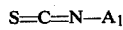

S=C=N—$A_1$   VI (wherein $A_1$ is as hereinbefore defined) with 3-(2-hydroxyethyl)-1,2,3,4-tetrahydroisoquinoline. The reaction is generally carried out in an organic solvent such as an alcohol, e.g. ethanol, at a temperature between 20° and 60° C.

The isothiocyanates of general formula VI (wherein $A_1$ is as hereinbefore defined) can be prepared by the reaction of carbon disulphide with a 5-aminoisoquinoline of the general formula:

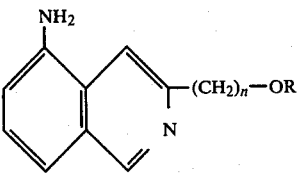

VII (wherein R and n are as hereinbefore defined) followed by the addition of dicyclohexylcarbodiimide. The condensation is generally carried out in the presence of a base such as a tertiary amine, e.g. triethylamine. The reaction is advantageously carried out in an organic solvent, such as pyridine, at a temperature between −10° and 25° C.

The 5-aminoisoquinoline derivatives of general formula VII can be obtained from a 3-alkoxyalkylisoquinoline of the general formula:

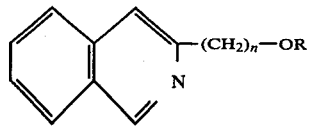

VIII (wherein R and n are as hereinbefore defined) by applying the method of N. P. Buu-Hoï et al., J. Chem. Soc., 3924 (1964).

The isoquinoline derivatives of general formula VIII can be prepared by reacting an appropriate alkali metal alkoxide with a hydrohalide of a 3-halogenoalkylisoquinoline of the general formula:

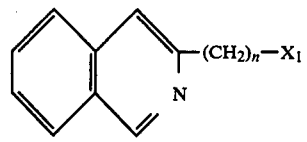

IX wherein n is as hereinbefore defined and $X_1$ represents a chlorine or bromine atom. The reaction is generally carried out in solution in the corresponding alcohol ROH (wherein R is as hereinbefore defined) at a temperature between 20° C. and the reflux temperature of the reaction mixture.

The hydrohalides of the 3-halogenoalkylisoquinolines of general formula IX can be prepared by halogenating a 3-hydroxyalkylisoquinoline of the general formula:

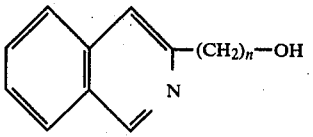

X wherein n is as hereinbefore defined.

Chlorination is generally carried out by the action of thionyl chloride at a temperature between 25° C. and the reflux temperature of the reaction mixture. Bromination is generally carried out by the action of a concentrated aqueous solution of hydrobromic acid at a temperature between 50° C. and the reflux temperature of the reaction mixture.

3-Hydroxymethylisoquinoline can be prepared in accordance with the method described by B. R. Brown et al., J. Chem. Soc., 1145 (1951).

3-(2-Hydroxyethyl)isoquinoline can be prepared in accordance with the method described in Japanese Patent Publication 53/127483 (Derwent CPI 90295 A).

The isoquinoline derivative of general formula VIII wherein the symbol n represents 2 can also be obtained by hydrogenating an enol ether of the general formula:

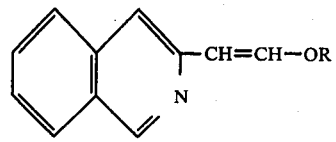

XI wherein R is as hereinbefore defined. The hydrogenation is generally carried out in the presence of palladium-on-charcoal as catalyst in an organic solvent, such as an alcohol (e.g. methanol or ethanol), at a temperature of about 20° C. under a pressure of about 15 atmospheres.

The enol ethers of general formula XI can be prepared by means of a Wittig reaction by condensing a phosphorane of the general formula:

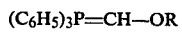

$(C_6H_5)_3P=CH-OR$    XII (wherein R is as hereinbefore defined) with 3-formylisoquinoline, under the conditions described by A. Maercker, Organic Reactions, 14, 270 (1965).

3-Formylisoquinoline can be obtained in accordance with the method described by J. Teague, J. Amer. Chem. Soc., 73, 688 (1951).

The phosphoranes of general formula XII can be prepared by treating the corresponding phosphonium bromide or chloride with a base, for example treatment with sodium methoxide in methanol or treatment with butyllithium in diethyl ether or tetrahydrofuran.

3-(2-Hydroxyethyl)-1,2,3,4-tetrahydroisoquinoline can be prepared from 3-hydroxymethyl-1,2,3,4-tetrahydroisoquinoline in accordance with the method described by T. A. Crabb et al., J. C. S. Perkin II, 370 (1977).

3-Hydroxymethyl-1,2,3,4-tetrahydroisoquinoline can be prepared from phenylalanine in accordance with the method described by S. Yamada and T. Kunieda, Chem. Pharm. Bull., 15,490 (1967).

When L-phenylalanine is used, the isoquinoline product of general formula III is obtained in the (S) form.

When D-phenylalanine is used, the isoquinoline product of general formula III is obtained in the (R) form.

When D,L-phenylalanine is used, the isoquinoline product of general formula III is obtained in the (RS) form.

According to a further feature of the invention, the isoquinoline derivatives of general formula III are prepared by the process which comprises reacting a amine of the general formula:

$A_1-NH_2$    XIII (wherein $A_1$ is as hereinbefore defined) with a salt of the general formula:

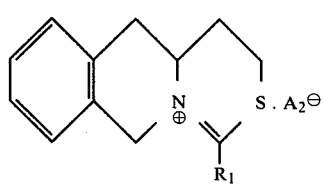

XIV wherein $R_1$ represents a chlorine atom, an alkylthio radical containing 1 to 4 carbon atoms (preferably methylthio), or a benzylthio radical, and $A_2^\ominus$ represents an anion, such as a chloride, iodide, sulphate, tetrafluoroborate or fluorosulphonate ion. When $R_1$ represents a chlorine atom, $A_2^\ominus$ represents a chloride ion. When $R_1$ represents an alkylthio or benzylthio radical, $A_2^\ominus$ represents an iodide, sulphate, tetrafluoroborate or fluorosulphate ion.

When $R_1$ represents a chlorine atom and $A_2^\ominus$ represents a chloride ion, the reaction is preferably carried out in an organic solvent, such as acetonitrile, in the presence of an alkaline condensing agent, such as triethylamine, at a temperature of about 20° C.

When $R_1$ represents an alkylthio or benzylthio radical and $A_2^\ominus$ represents an iodide, sulphate, tetrafluoroborate or fluorosulphonate ion, the reaction is preferably carried out in a basic organic solvent, such as pyridine, at a temperature between 30° and 50° C.

The salt of the general formula XIV wherein $R_1$ represents a chlorine atom and $A_2^\ominus$ represents a chloride ion can be obtained by the reaction of a chlorinating agent, such as phosgene, phosphorus pentachloride, thionyl chloride or oxalyl chloride, with 1,6,11,11a-tetrahydro[1,3-thiazino][3,4-b]isoquinoline-4-thione of the formula:

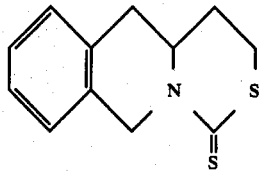

XV

The reaction is generally carried out in an organic solvent or in a mixture of organic solvents, such as a mixture of toluene and tetrahydrofuran, at a temperature between 0° and 70° C.

The salts of general formula XIV wherein $R_1$ represents an alkylthio or benzylthio radical and $A_2^\ominus$ represents an iodide, sulphate, tetrafluoroborate or fluorosulphonate ion can be obtained by the action of a reactive ester of the general formula:

$$R_2-A_3 \qquad \qquad XVI$$

(wherein $R_2$ represents an alkyl radical containing 1 to 4 carbon atoms or a benzyl radical, and $A_3$ represents the residue of a reactive ester such as an iodine atom or an alkoxysulphonyloxy radical), or by the action of triethyloxonium tetrafluoroborate or methyl fluorosulphonate, on a compound of formula XV. The reaction is generally carried out, optionally in the presence of an organic solvent, such as methylene chloride, chloroform or dichloroethane, at a temperature of about 20° C.

1,6,11,11a-Tetrahydro[1,3-thiazino][3,4-b]isoquinoline-4-thione can be prepared by reacting 3-(2-hydroxyethyl)-1,2,3,4-tetrahydroisoquinoline successively with carbon disulphate in the presence of a base and then which methanesulphonyl chloride or tosyl chloride, followed by cyclisation of the intermediate obtained.

The carbon disulphide is generally reacted with the tetrahydroisoquinoline in the presence of a base such as a tertiary amine, e.g. triethylamine.

The successive reaction of carbon disulphide and then methanesulphonyl chloride or tosyl chloride is advantageously carried out in an organic solvent, such as pyridine, at a temperature between −10° and 20° C.

The cyclisation of the intermediate is generally carried out by heating in an organic solvent, such as dimethylformamide or in a mixture of organic solvents (for example dimethylformamide and pyridine), at a temperature between 50° and 100° C. It is not necessary to isolate the intermediate in order to perform this cyclisation.

The isoquinoline derivatives of general formula III may be converted by known methods into acid addition salts. (By the term "known methods" is meant methods heretofore used or described in the chemical literature). The acid addition salts may be obtained by reacting the isoquinoline derivatives with acids is appropriate solvents. As organic solvents there may be used alcohols, ketones, ethers or chlorinated hydrocarbons. The salt which is formed is precipitated, if necessary after concentration of the solution, and is isolated by filtration or decantation.

The isoquinoline derivatives of general formula III and/or their acid addition salts can optionally be purified by physical methods such as crystallisation or chromatography.

The isoquinoline derivatives of general formula III and their acid addition salts possess useful pharmacological properties as analgesic agents. Some of them are also particularly active as anti-inflammatory and antipyretic agents.

The analgesic activity manifests itself in mice at doses of between 0.4 and 10 mg/kg animal body weight, administered orally, using the technique of Siegmund et al., Proc. Soc. Exp. Biol. Med., 95, 729 (1957).

The anti-inflammatory activity of some of the products manifests itself in rats at doses of between 0.5 and 50 mg/kg animal body weight, administered orally, using the technique of K. F. Benitz and L. M. Hall, Arch. Int. Pharmacodyn., 144, 185 (1963).

The antipyretic activity of some of these products manifests itself in rats at doses of between 0.4 and 10 mg/kg animal body weight, administered orally, using the technique of J. J. Loux et al., Toxicol. Appl. Pharmacol., 22, 674 (1972).

Furthermore, the isoquinoline derivatives of the present invention are of very low toxicity. Their acute toxicity in mice, expressed as their $LD_{50}$, is more than 900 mg/kg animal body weight, administered orally.

Of particular value as analgesic agents are the isoquinoline derivatives of the general formula:

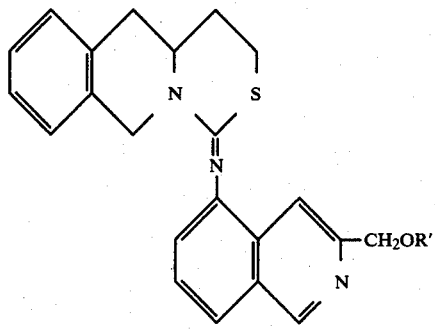

XVII wherein R′ represents a straight- or branched-chain alkyl radical containing 1 to 4 carbon atoms, and more especially (RS)-4-[(3-methoxymethylisoquinol-5- yl)imino]-1,6,11,11a-tetrahydro[1,3-thiazino][3,4-b]isoquinoline, (RS)-4-[(3ethoxymethylisoquinol-5-yl)-imino]-1,6,11,11a-tetrahydro[1,3-thiazino][3,4-b]isoquinoline and (RS)-4-[(3-propoxymethylisoquinol-5-yl)imino]-1,6,11,11a-tetrahydro[1,3-thiazino][3,4-b]isoquinoline. Amongst the aforementioned compounds, the 3-methoxymethyl compound in particular also possesses a good anti-inflammatory activity and the 3-propoxymethyl compound in particular also possesses a good antipyretic activity.

For therapeutic purposes the isoquinoline derivatives of general formula III are employed as such or in the form of pharmaceutically acceptable salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of the new isoquinoline derivatives of the present invention.

EXAMPLE 1

(RS)-3-(2-Hydroxyethyl)-N-(3-methoxymethylisoquinol-5-yl)-1,2,3,4-tetrahydroisoquinoline-2-carbothioamide (20.9 g) is heated for 2 hours at 100° C. in 6 N hydrochloric acid (200 cc). The solution is evaporated to dryness at 60° C. under reduced pressure (40 mm Hg). The residue is taken up in 2 N sodium hydroxide solution (250 cc) and extraction is carried out with methylene chloride (3×200 cc). The organic extracts are combined, washed with water (50 cc) and dried over magnesium sulphate. After filtration, the filtrate is evaporated to dryness at 40° C. under reduced pressure (20 mm Hg). The residue is recrystallised from ethanol (250 cc). (RS)-4-[(3-Methoxymethylisoquinol-5-yl)imino]-1,6,11,11a-tetrahydro[1,3-thiazino][3,4-b]isoquinoline (15.6 g), m.p. 135° C., is thus obtained.

(RS)-3-(2-Hydroxyethyl)-N-(3-methoxymethylisoquinol-5-yl)-1,2,3,4-tetrahydroisoquinoline-2-carbothioamide can be prepared in the following manner:

5-Isothiocyanato-3-methoxymethylisoquinoline (18.2 g) is added to a solution of (RS)-3-(2-hydroxyethyl)-1,2,3,4-tetrahydroisoquinoline (14 g) in ethanol (250 cc). The mixture is stirred for 24 hours at a temperature of about 20° C. The precipitate formed is filtered off and washed with ethanol (2×10 cc) and diethyl ether (2×10 cc). (RS)-3-(2-Hydroxyethyl)-N-(3-methoxymethylisoquinol-5-yl)-1,2,3,4-tetrahydroisoquinoline-2-carbothioamide (20.9 g), m.p. 152° C., is thus obtained.

(RS)-3-(2-Hydroxyethyl)-1,2,3,4-tetrahydroisoquinoline can be prepared as described in Belgian Patent No. 871890.

5-Isothiocyanato-3-methoxymethylisoquinoline can be prepared in the following manner:

A solution of 5-amino-3-methoxymethylisoquinoline (22.9 g) in pyridine (80 cc) is added dropwise, whilst stirring and at a temperature of about −10° C., to a solution of triethylamine (17 cc) and carbon disulphide (55 cc) in pyridine (80 cc). After 4 hours at −10° C., a solution of dicyclohexylcarbodiimide (25.2 g) in pyridine (80 cc) is added dropwise. Stirring is maintained for 3 hours at a temperature which changes from −10° to 20° C., and then for 20 hours at a temperature of about 20° C. The mixture is evaporated to dryness at 60° C. under reduced pressure (20 mm Hg), the residue is taken up in methylene chloride (800 cc), and insoluble material is removed by filtration and the filtrate is evaporated to dryness at 40° C. under reduced pressure (40 mm Hg). The residue is taken up in diisopropyl ether (1 liter; an insoluble material is removed by filtration and the filtrate is evaporated to dryness at 40° C. under reduced pressure (20 mm Hg). 5-Isothiocyanato-3-methoxymethylisoquinoline (18.5 g), m.p. 88° C., is obtained.

5-Amino-3-methoxymethylisoquinoline can be prepared in the following manner:

A catalyst (3% palladium-on-charcoal; 8 g) is added to a solution of 3-methoxymethyl-5-nitroisoquinoline (78 g) in ethanol (2 liters). The resulting suspension is stirred and hydrogen is bubbled through for 6 hours, whilst keeping the temperature between 20° and 25° C. with the aid of a cold-water bath. The reaction mixture is filtered and the filtrate is evaporated to dryness at 60° C. under reduced pressure (20 mm Hg). The residue is recrystallised from diisopropyl ether (500 cc). 5-Amino-3-methoxymethylisoquinoline (47 g), m.p. 105° C., is obtained.

3-Methoxymethyl-5-nitroisoquinoline can be prepared in the following manner:

3-Methoxymethylisoquinoline (68.8 g) is dissovled in 95% sulphuric acid (density 1.83; 300 cc). The solution is cooled to 0° C. and a mixture of 70% nitric acid (density 1.42; 25 cc) and 95% sulphuric acid (density 1.83; 100 cc) is added dropwise in the course of 30 minutes so as not to exceed 10° C. Stirring is continued for 16 hours, whilst allowing the temperature to return to about 20° C. The mixture is then poured into a mixture of ice and water (2 liters), and an ammonia solution containing 20% of $NH_3$ (density 0.9) is added, without exceeding 30° C., until a pH of about 10 is obtained. The resulting yellow solution is extracted with methylene chloride (4×400 cc). The organic extracts are combined, washed with water (2×50 cc), dried over magnesium sulphate and filtered and the filtrate is evaporated to dryness at 40° C. under reduced pressure (20 mm Hg). 3-Methoxymethyl-5-nitroisoquinoline (78 g), m.p. 91° C., is obtained.

3-Methoxymethylisoquinoline can be prepared in the following manner:

A mixture of 3-chloromethylisoquinoline hydrochloride (96 g) and sodium methoxide (80 g) in methanol (1.5 liters) is heated under reflux for 8 hours. After cooling to 20° C., the mixture is filtered and the filtrate is evaporated to dryness at 50° C. under reduced pressure (20 mm Hg). The residue is taken up in methylene chloride (1 liter), the mixture is washed with water (3×150 cc), the organic phase is dried over magnesium sulphate and filtered, and the filtrate is evaporated to dryness at 40° C. under reduced pressure (20 mm Hg). The oily residue is distilled at 82° C. under reduced pressure (0.6 mm Hg). 3-Methoxymethylisoquinoline (68 g), a colourless oil, is obtained.

3-Chloromethylisoquinoline hydrochloride can be prepared in the following manner:

3-Hydroxymethylisoquinoline (110 g) is added to thionyl chloride (130 cc), whilst cooling so as to keep the temperature between 25° and 30° C. The reaction mixture is then heated to the reflux temperature at a rate which is such that the evolution of gas is not excessive. The mixture is heated under reflux for 90 minutes (until the evolution of gas ceases) and then for a further 30 minutes. It is then cooled to 5° C. with ice, the slurry formed is filtered and the solid is washed with diethyl ether. 3-Chloromethylisoquinoline hydrochloride (136 g), m.p. 202° C., is obtained.

3-Hydroxymethylisoquinoline can be prepared by the method described by B. R. Brown et al., J. Chem. Soc., 1145 (1951).

EXAMPLE 2

By following the procedure of Example 1 but using (RS)-3-(2-hydroxyethyl)-N-(3-ethoxymethylisoquinol-5-yl)-1,2,3,4-tetrahydroisoquinoline-2-carbothioamide (9 g) in 6 N hydrochloric acid (50 cc), (RS)-4-[(3-ethoxymethylisoquinol-5-yl)imino]-1,6,11,11a-tetrahydro[1,3-thiazino][3,4-b]isoquinoline (4.8 g), m.p. 89° C., is obtained.

(RS)-3-(2-Hydroxyethyl)-N-(3-ethoxymethylisoquinol-5-yl)-1,2,3,4-tetrahydroisoquinoline-2-carbothioamide can be prepared in a manner similar to that described in Example 1 for the homologous compound using 3-ethoxymethyl-5-isothiocyanatoisoquinoline (7 g) and (RS)-3-(2-hydroxyethyl)-1,2,3,4-tetrahydroisoquinoline (5 g) in ethanol (80 cc). A product (9 g) melting at 147° C. is obtained.

3-Ethoxymethyl-5-isothiocyanatoisoquinoline can be prepared in a manner similar to that described in Example 1 for the homologous compound by reacting 5-amino-3-ethoxymethylisoquinoline (6.5 g) with carbon disulphide (16 cc), triethylamine (4.5 cc) and dicyclohexylcarbodiimide (6.6 g) in pyridine. A product (7 g) melting at 66° C. is obtained.

5-Amino-3-ethoxymethylisoquinoline can be prepared in a manner similar to that described in Example 1 for the homologous compound by hydrogenating 3-ethoxymethyl-5-nitroisoquinoline (24 g) in ethanol (350 cc) in the presence of a catalyst (3% palladium-on-charcoal; 3.5 g). A product (16.5 g) melting at 95° C. is obtained.

3-Ethoxymethyl-5-nitroisoquinoline can be prepared in a manner similar to that described in Example 1 for the homologous compound by nitrating 3-ethoxymethylisoquinoline (31 g) with 70% nitric acid (10.2 cc) in 95% sulphuric acid (135 cc). A product (24 g) melting at 54° C. is obtained.

3-Ethoxymethylisoquinoline can be prepared in a manner similar to that described in Example 1 for the homologous compound by reacting sodium ethoxide (40 g) with 3-chloromethylisoquinoline hydrochloride (40 g) in ethanol (700 cc). A pale yellow oil (31 g) distilling at 110°–114° C. under a pressure of 0.6 mm Hg is obtained.

EXAMPLE 3

By following the procedure of Example 1 but using (RS)-3-(2-hydroxyethyl)-N-(3-propoxymethylisoquinol-5-yl)-1,2,3,4-tetrahydroisoquinoline-2-carbothioamide (4.5 g) in 6 N hydrochloric acid (50 cc), an oil (3.5 g) is obtained. This product is dissolved in ethanol (50 cc), and a 4 N solution of hydrogen chloride in diethyl ether (10 cc) is added. The crystals formed are isolated on a filter, washed with ethanol and dried. (RS)-4-[(3-Propoxymethylisoquinol-5-yl)imino]1,6,11,-11a-tetrahydro[1,3-thiazino][3,4-b]isoquinoline hydrochloride (3.9 g), m.p. 175° C., is obtained.

(RS)-3-(2-Hydroxyethyl)-N-(3-propoxymethylisoquinol-5-yl)-1,2,3,4-tetrahydroisoquinoline-2-carbothioamide can be prepared in a manner similar to that described in Example 1 for the homologous compound using 5-isothiocyanato-3-propoxymethylisoquinoline (5.2 g) and (RS)-3-(2-hydroxyethyl)-1,2,3,4-tetrahydroisoquinoline (3.6 g) in ethanol (50 cc). A product (3.1 g) melting at 122° C. is obtained.

5-Isothiocyanato-3-propoxymethylisoquinoline can be prepared in a manner similar to that described in Example 1 for the homologous compound by reacting 5-amino-3-propoxymethylisoquinoline (20.3 g) with carbon disulphide (40 cc), triethylamine (13 cc) and dicyclohexylcarbodiimide (19.4 g) in pyridine. An oily product (7.7 g) is obtained.

5-Amino-3-propoxymethylisoquinoline can be obtained in a manner similar to that described in Example 1 for the homologous compound by hydrogenating 5-nitro-3-propoxymethylisoquinoline (23.1 g) in ethanol (500 cc) in the presence of a catalyst (3% palladium-on-charcoal; 2.5 g). A product (21 g) is obtained.

5-Nitro-3-propoxymethylisoquinoline can be obtained in a manner similar to that described in Example 1 for the homologous compound by nitrating 3-propoxymethylisoquinoline (28.2 g) with 70% nitric acid (8.7 cc) in 95% sulphuric acid (250 cc). An oily product (16.5 g) is obtained.

3-Propoxymethylisoquinoline can be prepared in a manner similar to that described in Example 1 for the homologous compound by reacting sodium propoxide (32.8 g) with 3-chloromethylisoquinoline hydrochloride (36 g) in propanol (500 cc). A pale yellow oil (28.5 g) distilling at 98°–102° C. under a pressure of 0.35 mm Hg is obtained.

EXAMPLE 4

By following the procedure of Example 1 but using (RS)-3-(2-hydroxyethyl)-N-(3-butoxymethylisoquinol-5-yl)-1,2,3,4-tetrahydroisoquinoline-2-carbothioamide (1 g) in 6 N hydrochloric acid (10 cc), an oily product (0.8 g) is obtained. This product is dissolved in ethanol (5 cc), fumaric acid (0.22 g) is added and the mixture is cooled to 0° C. The crystals formed are filtered off, washed with ethanol and dried. (RS)-4-[(3-Butoxymethylisoquinol-5-yl)imino]1,6,11,11a-tetrahydro[1,3-thiazino][3,4-b]isoquinoline fumarate (0.28 g), m.p. 139° C., is obtained.

(RS)-3-(2-Hydroxyethyl)-N-(3-butoxymethylisoquinol-5-yl)-1,2,3,4-tetrahydroisoquinoline-2-carbothioamide can be prepared in a manner similar to that described in Example 1 for the homologous compound using 3-butoxymethyl-5-isothiocyanatoisoquinoline (5.5 g) and (RS)-3-(2-hydroxyethyl)-1,2,3,4-tetrahydroisoquinoline (3.5 g) in ethanol (50 cc). An amorphous solid product (1.1 g) is obtained.

3-Butoxymethyl-5-isothiocyanatoisoquinoline can be prepared in a manner similar to that described in Example 1 for the homologous compound by reacting 5-amino-3-butoxymethylisoquinoline (18.3 g) with carbon disulphide (40 cc), triethylamine (11 cc) and dicyclohexylcarbodiimide (16.4 g) in pyridine (160 cc). An oily product (11.1 g) is obtained.

5-Amino-3-butoxymethylisoquinoline can be obtained in a manner similar to that described in Example 1 for the homologous compound by hydrogenating 3-butoxymethyl-5-nitroisoquinoline (20.7 g) in ethanol (500 cc) in the presence of a catalyst (3% palladium-on-charcoal; 7.5 g). A product (19.7 g) is obtained.

3-Butoxymethyl-5-nitroisoquinoline can be obtained in a manner similar to that described in Example 1 for the homologous compound by nitrating 3-butoxymethylisoquinoline (29 g) with 70% nitric acid (8.4 cc) in 95% sulphuric acid (250 cc). An oily product (17.8 g) is obtained.

3-Butoxymethylisoquinoline can be prepared in a manner similar to that described in Example 1 for the homologous compound by reacting sodium butoxide (37.6 g) with 3-chloromethylisoquinoline hydrochloride (36 g) in butanol (500 cc). A pale yellow oil (29 g) distilling at 112°–114° C. under a pressure of 0.3 mm Hg is obtained.

EXAMPLE 5

By following the procedure of Example 1 but using (RS)-3-(2-hydroxyethyl)-N-(3-octyloxymethylisoquinol-5-yl)-1,2,3,4-tetrahydroisoquinoline-2-carbothioamide (2.3 g) in 6 N hydrochloric acid (30 cc), (RS)-4-[(3-octyloxymethylisoquinol-5-yl)imino]-1,6,11,11a-tetrahydro[1,3-thiazino][3,4-b]isoquinoline (1 g), m.p. 85° C., is obtained.

(RS)-3-(2-Hydroxyethyl)-N-(3-octyloxymethylisoquinol-5-yl)-1,2,3,4-tetrahydroisoquinoline-2-carbothioamide can be obtained in a manner similar to that described in Example 1 for the homologous compound using 5-isothiocyanato-3-octyloxymethylisoquinoline (3.3 g) and (RS)-3-(2-hydroxyethyl)-1,2,3,4-tetrahydroisoquinoline (1.8 g) in ethanol (40 cc). A product (2.3 g) melting at 122° C. is obtained.

5-Isothiocyanato-3-octyloxymethylisoquinoline can be prepared in a manner similar to that described in Example 1 for the homologous compound by reacting 5-amino-3-octyloxymethylisoquinoline (10.3 g) with carbon disulphide (15 cc), triethylamine (5 cc) and dicyclohexylcarbodiimide (7.4 g) in pyridine. An oily product (11.3 g) is obtained.

5-Amino-3-octyloxymethylisoquinoline can be prepared in a manner similar to that described in Example 1 for the homologous compound by hydrogenating 5-nitro-3-octyloxymethylisoquinoline (12.7 g) in ethanol (300 cc) in the presence of a catalyst (3% palladium-on-charcoal; 1.4 g). A product (10.3 g) is obtained.

5-Nitro-3-octyloxymethylisoquinoline can be prepared in a manner similar to that described in Example 1 for the homologous compound by nitrating 3-octyloxymethylisoquinoline (22.5 g) with 70% nitric acid (5.1 cc) in 95% sulphuric acid (125 cc). An oily product (13.4 g) is obtained.

3-Octyloxymethylisoquinoline can be prepared in a manner similar to that described in Example 1 for the homologous compound by reacting sodium octoxide (42.6 g) with 3-chloromethylisoquinoline hydrochloride (21.4 g) in octanol (250 cc). A pale yellow oil (23 g) distilling at 172°–176° C. under a pressure of 0.6 mm Hg is obtained.

EXAMPLE 6

By following the procedure of Example 1 but using (RS)-3-(2-hydroxyethyl)-N-[3-(2-methoxyethyl)isoquinol-5-yl]-1,2,3,4-tetrahydroisoquinoline-2-carbothioamide (0.4 g) in 6 N hydrochloric acid (5 cc), (RS)-4-{[3-(2-methoxyeythyl)isoquinol-5-yl]imino}-1,6,11,11a,-tetrahydro[1,3-thiazino][3,4-b]isoquinoline (0.1 g), an amorphous solid, is obtained. Mass spectrum: m/e=403.

(RS)-3-(2-Hydroxyethyl)-N-[3-(2-methoxyethyl)isoquinol-5-yl]-1,2,3,4-tetrahydroisoquinoline-2-carbothioamide can be prepared in a manner similar to that described in Example 1 for the homologous compound using 5-isothiocyanato-3-(2-methoxyethyl)isoquinoline (0.7 g) and (RS)-3-(2-hydroxyethyl)-1,2,3,4-tetrahydroisoquinoline (0.55 g) in ethanol (10 cc). A product (0.4 g) is obtained. 5-Isothiocyanato-3-(2-methoxyethyl)-isoquinoline can be prepared in a manner similar to that described in Example 1 for the homologous compound by reacting 5-amino-3-(2-methoxyethyl)-isoquinoline (0.8 g) with carbon disulphide (1.6 cc), triethylamine (0.5 cc) and dicyclohexylcarbodiimide (0.8 g) in pyridine. A product (0.7 g) is obtained.

5-Amino-3-(2-methoxyethyl)isoquinoline can be prepared in a manner similar to that described in Example 1 for the homologous compound by hydrogenating 3-(2-methoxyethyl)-5-nitroisoquinoline (0.9 g) in ethanol (10 cc) in the presence of a catalyst (3% palladium-on-charcoal; 0.1 g). A product (0.8 g) is obtained.

3-(2-Methoxyethyl)-5-nitroisoquinoline can be obtained in a manner similar to that described in Example 1 for the homologous compound by nitrating 3-(2-methoxyethyl)isoquinoline (2.1 g) with 70% nitric acid (0.7 cc) in 95% sulphuric acid (30 cc). A product (0.95 g) is obtained.

3-(2-Methoxyethyl)isoquinoline can be obtained in the following manner:

3-(2-Methoxyvinyl)isoquinoline (a mixture of the cis and trans isomers; 5 g) is dissolved in methanol (50 cc). A catalyst (3% palladium-on-carbon; 0.5 g) is added and the mixture is hydrogenated in an autoclave at 20° C. under a pressure of 15 atmospheres for 20 hours, whilst stirring. The reaction mixture is then filtered and the filtrate is concentrated to dryness at 40° C. under reduced pressure (20 mm Hg). The oily residue is dissolved in methylene chloride (10 cc) and the solution is poured into a column (diameter 2 cm) containing silica (100 g) in methylene chloride. Elution is carried out with a 99-1 (by volume) methylene chloridemethanol mixture (2 liters), 100 cc fractions being collected. Fractions 10 to 15 are combined and concentrated to dryness at 40° C. under reduced pressure (20 mm Hg). 3-(2-Methoxyethyl)isoquinoline (2.1 g) is obtained in the form of an oil.

3-(2-Methoxyvinyl)isoquinoline can be obtained in the following manner:

Methoxymethyltriphenylphosphonium chloride (33.9 g) is dissolved in methanol (150 cc), and a solution of sodium methoxide (4.5 g) in methanol (60 cc) is added. The mixture is stirred for 30 minutes at 20° C. and 3-formylisoquinoline (14.1 g) is then added. The mixture is stirred under reflux for 4 hours and then concentrated to dryness at 40° C. under reduced pressure (20 mm Hg). The residue is taken up in diethyl ether (400 cc). An insoluble material is filtered off and the filtrate is concentrated to dryness at 40° C. under reduced pressure (20 mm Hg). The residue is chromatographed on silica (500 g) contained in a column of diameter 3 cm. Elution is carried out with a 99-1 (by volume) methylene chloride-methanol mixture (3 liters), 150 cc fractions being collected. Fractions 8 to 16 are combined and concentrated to dryness at 40° C. under reduced pressure (20 mm Hg). A mixture of the cis and trans isomers of 3-(2-methoxyvinyl)isoquinoline (9.9 g) is obtained in the from of a yellow oil.

The present invention includes within its scope pharmaceutical compositions comprising, as active ingredient, at least one of the compounds of general formula II, or a non-toxic acid addition salt thereof, in association with a pharmaceutical carrier or coating. The invention includes especially such preparations made up for oral, parenteral, rectal or topical administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The compositions for topical application are, in particular, creams or ointments.

The pharmaceutical compositions according to the invention are particularly useful in human therapy for their anti-inflammatory, analgesic and antipyretic action. They are particularly indicated for the treatment of inflammatory diseases (ankylosing spondylarthritis, acute articular rheumatism and arthrosis), acute and chronic pains, rheumatic and traumatic algias, dental, neurological and visceral pains, various algias (pains experienced by cancer patients), febrile conditions, and medical, surgical and obstetrical complaints giving rise to thromboses and embolisms.

In human therapy, the doses depend on the desired effect and the duration of the treatment; for an adult, they are generally between 100 and 2000 mg per day.

In general, the physician will decide the posology considered most appropriate, taking into account the age, weight and other factors intrinsic to the patient being treated.

The following Example illustrates pharmaceutical compositions according to the invention.

EXAMPLE 7

Tablets containing 100 mg doses of active product and having the following composition are prepared in accordance with the usual technique:

| | |
|---|---|
| (RS)-3-[(3-methoxymethylisoquinol-5-yl)- imino]-1,6,11,11a-tetrahydro[1,3-thiazino]- | |
| [3,4-b]isoquinoline | 0.100 g |
| starch | 0.110 g |
| precipitated silica | 0.035 g |
| magnesium stearate | 0.005 g |

We claim:

1. An isoquinoline derivative of the formula:

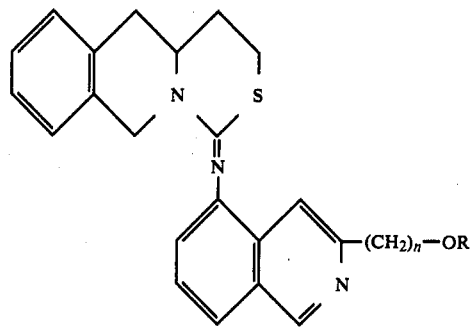

wherein R represents alkyl of 1 through 8 carbon atoms and n represents 1 or 2, and its non-toxic pharmaceutically acceptable acid addition salts.

2. An isoquinoline derivative according to claim 1 wherein R represents alkyl of 1 through 4 carbon atoms and n represents 1, and its non-toxic pharmaceutically acceptable acid addtion salts.

3. The isoquinoline derivative according to claim 1 which is (RS)-4-[(3-methoxymethylisoquinol-5-yl)imino]-1,6,11,11a-tetrahydro[1,3-thiazino][3,4-d]isoquinoline and its non-toxic pharmaceutically acceptable acid addition salts.

4. The isoquinoline derivative according to claim 1 which is (RS)-4-[(3-ethoxymethylisoquinol-5-yl)imino]-1,6,11,11a-tetrahydro[1,3-thiazino][3,4-b]isoquinoline and its non-toxic pharmaceutically acceptable acid addition salts.

5. The isoquinoline derivative according to claim 1 which is (RS)-4-[(3-propoxymethylisoquinol-5-yl)imino]-1,6,11,11a-tetrahydro[1,3-thiazino][3,4-b]isoquinoline and its non-toxic pharmaceutically acceptable acid addition salts.

6. The isoquinoline derivative according to claim 1 which is (RS)-4-[(3-butoxymethylisoquinol-5-yl)imino]-1,6,11,11a-tetrahydro[1,3-thiazino][3,4-b]isoquinoline and its non-toxic pharmaceutically acceptable acid addition salts.

7. The isoquinoline derivative according to claim 1 which is (RS)-4-[(3-octyloxymethylisoquinol-5-yl)imino]-1,6,11,11a-tetrahydro[1,3-thiazino][3,4-b]isoquinoline and its non-toxic pharamceutically acceptable acid addition salts.

8. The isoquinoline derivative according to claim 1 which is (RS)-4-{[3-(2-methoxyethyl)isoquinol-5-yl]imino}-1,6,11,11-tetrahydro[1,3-thiazolino][3,4-b]isoquinoline and its non-toxic pharamceutically acceptable acid addition salts.

9. A pharmaceutical composition useful as an analgesic or—when appropriate—as an antiinflammatory or antipyretic which comprises as active ingredient an effective amount of an isoquinoline derivative of the formula depicted in claim 1, wherein R and n are as defined in claim 1, or a non-toxic pharmaceutically acceptable acid addition salt thereof, association with a significant amount of a pharmaceutically acceptable carrier.

* * * * *